(12) United States Patent
Bachmann et al.

(10) Patent No.: US 8,377,081 B2
(45) Date of Patent: *Feb. 19, 2013

(54) CLOSURE SYSTEM FOR TUBULAR ORGANS

(75) Inventors: Michel Bachmann, Vaux-sur-Morges (CH); Christian Imbert, Froideville (CH); Alain Jordan, Denges (CH)

(73) Assignee: Allergan, Inc., Irvine, CA (US)

( * ) Notice: Subject to any disclaimer, the term of this patent is extended or adjusted under 35 U.S.C. 154(b) by 60 days.

This patent is subject to a terminal disclaimer.

(21) Appl. No.: 12/874,147

(22) Filed: Sep. 1, 2010

(65) Prior Publication Data

US 2011/0040141 A1 Feb. 17, 2011

Related U.S. Application Data

(63) Continuation of application No. 10/591,869, filed as application No. PCT/IB2005/050822 on Mar. 5, 2005, now Pat. No. 7,811,299.

(51) Int. Cl.
A61B 17/08 (2006.01)
(52) U.S. Cl. ....................................................... 606/157
(58) Field of Classification Search ........................ None
See application file for complete search history.

(56) References Cited

U.S. PATENT DOCUMENTS

| | | | |
|---|---|---|---|
| 1,174,814 A | 3/1916 | Brennan et al. |
| 1,830,947 A | 11/1931 | Klingel |
| 1,999,683 A | 4/1935 | Borresen |
| 2,163,048 A | 6/1939 | McKee |
| 2,339,138 A | 1/1944 | Black |
| 2,405,667 A | 8/1946 | Ottesen |
| 2,438,231 A | 3/1948 | Schultz et al. |
| 2,635,907 A | 4/1953 | Heimbuch |
| 2,714,469 A | 8/1955 | Carlson |
| 2,936,980 A | 5/1960 | Rapata |
| 3,059,645 A | 10/1962 | Hasbrouck et al. |
| 3,189,961 A | 6/1965 | Heller |
| 3,667,081 A | 6/1972 | Burger |
| 3,840,018 A | 10/1974 | Heifetz |

(Continued)

FOREIGN PATENT DOCUMENTS

| | | |
|---|---|---|
| CA | 949965 | 6/1974 |
| CN | 1250382 | 4/2000 |

(Continued)

OTHER PUBLICATIONS

Acuna-Goycolea et al.; "Mechanism of Neuropeptide Y, Peptide YY, and Pancreatic Polypeptide Inhibition of Identified Green Fluorescent Protein-Expressing GABA Neurons in the Hypothalamic Neuroendocrine Acruate Nucleus"; The Journal of Neuroscience; V. 25(32); pp. 7406-7419; Aug. 10, 2005.

(Continued)

Primary Examiner — Melanie Tyson
Assistant Examiner — Son Dang
(74) Attorney, Agent, or Firm — Stephen Donovan; Debra Condino

(57) ABSTRACT

In one embodiment, a surgically implantable adjustable ring comprises a ring body, which includes a closure system having first and second end parts. The ring body is designed to be closed around a tubular organ by the closure system, constricting the tubular organ by forming a loop. The first end part is shaped like a sleeve having a first and second end portions, and is designed to receive the second end part of the ring. The sleeve is substantially perpendicular to the main direction of the first end part of the ring, and the second end part of the ring includes a locking protrusion adapted to hold the sleeve in position, securing the ring in a closed position by engaging the locking protrusion in an opening disposed on the sleeve.

19 Claims, 2 Drawing Sheets

U.S. PATENT DOCUMENTS

| | | | |
|---|---|---|---|
| 3,955,834 A | 5/1976 | Ahlrot |
| 4,053,176 A | 10/1977 | Hilbush |
| 4,118,805 A | 10/1978 | Reimels |
| 4,133,315 A | 1/1979 | Berman et al. |
| 4,157,713 A | 6/1979 | Clarey |
| 4,176,412 A | 12/1979 | Peterson |
| 4,236,521 A | 12/1980 | Lauterjung |
| 4,271,827 A | 6/1981 | Angelchik |
| 4,299,012 A | 11/1981 | Oetiker |
| 4,340,083 A | 7/1982 | Cummins |
| 4,399,809 A | 8/1983 | Baro et al. |
| 4,408,597 A | 10/1983 | Tenney, Jr. et al. |
| 4,417,567 A | 11/1983 | Trick |
| 4,424,208 A | 1/1984 | Wallace et al. |
| 4,442,153 A | 4/1984 | Meltsch |
| 4,450,375 A | 5/1984 | Siegal |
| 4,485,805 A | 12/1984 | Foster, Jr. |
| 4,492,004 A | 1/1985 | Oetiker |
| 4,551,862 A | 11/1985 | Haber |
| 4,558,699 A | 12/1985 | Bashour |
| 4,559,699 A | 12/1985 | Owen et al. |
| 4,582,640 A | 4/1986 | Smestad et al. |
| 4,582,865 A | 4/1986 | Balazs et al. |
| 4,592,339 A | 6/1986 | Kuzmak et al. |
| 4,592,355 A | 6/1986 | Antebi |
| 4,601,713 A | 7/1986 | Fuqua |
| 4,667,672 A | 5/1987 | Romanowski |
| 4,671,351 A | 6/1987 | Rappe |
| 4,693,695 A | 9/1987 | Cheng |
| 4,694,827 A | 9/1987 | Weiner et al. |
| 4,696,288 A | 9/1987 | Kuzmak et al. |
| 4,708,140 A | 11/1987 | Baron |
| 4,716,154 A | 12/1987 | Malson et al. |
| 4,753,086 A | 6/1988 | Schmidt |
| 4,760,837 A | 8/1988 | Petit |
| 4,803,075 A | 2/1989 | Wallace et al. |
| 4,881,939 A | 11/1989 | Newman |
| 4,883,467 A | 11/1989 | Franetzki et al. |
| 4,886,787 A | 12/1989 | de Belder et al. |
| 4,896,787 A | 1/1990 | Delamour et al. |
| 4,915,690 A | 4/1990 | Cone et al. |
| 4,925,446 A | 5/1990 | Garay et al. |
| 4,944,487 A | 7/1990 | Holtermann |
| 4,944,659 A | 7/1990 | Labbe et al. |
| 4,958,791 A | 9/1990 | Nakamura |
| 4,969,899 A | 11/1990 | Cox, Jr. |
| 4,994,019 A | 2/1991 | Fernandez et al. |
| 5,045,060 A | 9/1991 | Melsky et al. |
| 5,074,868 A | 12/1991 | Kuzmak |
| 5,084,061 A | 1/1992 | Gau et al. |
| 5,091,171 A | 2/1992 | Yu et al. |
| 5,116,652 A | 5/1992 | Alzner |
| 5,120,313 A | 6/1992 | Elftman |
| 5,143,724 A | 9/1992 | Leshchiner et al. |
| 5,152,770 A | 10/1992 | Bengmark et al. |
| 5,160,338 A | 11/1992 | Vincent |
| 5,188,609 A | 2/1993 | Bayless et al. |
| 5,224,494 A | 7/1993 | Enhorning |
| 5,226,429 A | 7/1993 | Kuzmak |
| 5,246,456 A | 9/1993 | Wilkinson |
| 5,246,698 A | 9/1993 | Leshchiner et al. |
| 5,259,399 A | 11/1993 | Brown |
| 5,326,349 A | 7/1994 | Baraff |
| 5,343,894 A | 9/1994 | Frisch et al. |
| 5,356,883 A | 10/1994 | Kuo et al. |
| 5,360,445 A | 11/1994 | Goldowsky |
| 5,391,156 A | 2/1995 | Hildwein et al. |
| 5,399,351 A | 3/1995 | Leshchiner et al. |
| 5,449,363 A | 9/1995 | Brust et al. |
| 5,449,368 A | 9/1995 | Kuzmak |
| 5,458,568 A | 10/1995 | Racchini et al. |
| 5,509,888 A | 4/1996 | Miller |
| 5,531,716 A | 7/1996 | Luzio et al. |
| 5,535,752 A | 7/1996 | Halperin et al. |
| 5,554,113 A | 9/1996 | Novak et al. |
| 5,562,714 A | 10/1996 | Grevious |
| 5,601,604 A | 2/1997 | Vincent |
| 5,607,418 A | 3/1997 | Arzbaecher |
| 5,633,001 A | 5/1997 | Agerup |
| 5,653,718 A | 8/1997 | Yoon |
| 5,658,298 A * | 8/1997 | Vincent et al. ............... 606/139 |
| 5,676,162 A | 10/1997 | Larson, Jr. et al. |
| 5,695,504 A | 12/1997 | Gifford, III et al. |
| 5,704,893 A | 1/1998 | Timm |
| 5,713,911 A | 2/1998 | Racenet et al. |
| 5,733,257 A | 3/1998 | Sternby |
| 5,748,200 A | 5/1998 | Funahashi |
| 5,766,232 A | 6/1998 | Grevious et al. |
| 5,769,877 A | 6/1998 | Barreras, Sr. |
| 5,785,295 A | 7/1998 | Tsai |
| 5,817,113 A | 10/1998 | Gifford, III et al. |
| 5,827,529 A | 10/1998 | Ono et al. |
| 5,833,698 A | 11/1998 | Hinchliffe et al. |
| 5,861,014 A | 1/1999 | Familoni |
| RE36,176 E | 3/1999 | Kuzmak |
| 5,886,042 A | 3/1999 | Yu et al. |
| 5,904,697 A | 5/1999 | Gifford, III et al. |
| 5,910,149 A | 6/1999 | Kuzmak |
| 5,928,195 A | 7/1999 | Malamud et al. |
| 5,938,669 A | 8/1999 | Klaiber et al. |
| 5,944,696 A | 8/1999 | Bayless et al. |
| 5,944,751 A | 8/1999 | Laub |
| 5,993,473 A | 11/1999 | Chan et al. |
| 6,013,679 A | 1/2000 | Kuo et al. |
| 6,024,340 A | 2/2000 | Lazarus et al. |
| 6,024,704 A | 2/2000 | Meador et al. |
| 6,048,309 A | 4/2000 | Flom et al. |
| 6,067,991 A | 5/2000 | Forsell |
| 6,074,341 A | 6/2000 | Anderson et al. |
| 6,074,378 A | 6/2000 | Mouri et al. |
| 6,083,249 A | 7/2000 | Familoni |
| 6,090,131 A | 7/2000 | Daley |
| 6,102,678 A | 8/2000 | Peclat |
| 6,102,922 A | 8/2000 | Jakobsson et al. |
| 6,171,321 B1 | 1/2001 | Gifford, III et al. |
| 6,193,734 B1 | 2/2001 | Bolduc et al. |
| 6,203,523 B1 | 3/2001 | Haller et al. |
| 6,210,345 B1 | 4/2001 | Van Brunt |
| 6,210,347 B1 | 4/2001 | Forsell |
| 6,221,024 B1 | 4/2001 | Miesel |
| 6,224,857 B1 | 5/2001 | Romeo et al. |
| 6,306,088 B1 | 10/2001 | Krausman et al. |
| 6,327,503 B1 | 12/2001 | Familoni |
| 6,371,965 B2 | 4/2002 | Gifford, III et al. |
| 6,372,494 B1 | 4/2002 | Naughton et al. |
| 6,383,218 B1 | 5/2002 | Sourdille et al. |
| 6,383,219 B1 | 5/2002 | Telandro et al. |
| 6,387,105 B1 | 5/2002 | Gifford, III et al. |
| 6,417,750 B1 | 7/2002 | Shon |
| 6,418,934 B1 | 7/2002 | Chin |
| 6,419,696 B1 | 7/2002 | Ortiz et al. |
| 6,432,040 B1 | 8/2002 | Meah |
| 6,439,539 B1 | 8/2002 | Powell |
| 6,443,957 B1 | 9/2002 | Addis |
| 6,443,965 B1 | 9/2002 | Gifford, III et al. |
| 6,450,173 B1 | 9/2002 | Forsell |
| 6,450,946 B1 | 9/2002 | Forsell |
| 6,451,034 B1 | 9/2002 | Gifford, III et al. |
| 6,453,907 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,454,785 B2 | 9/2002 | De Hoyos Garza |
| 6,457,801 B1 | 10/2002 | Fish et al. |
| 6,460,543 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |
| 6,474,584 B2 | 11/2002 | Ekich |
| 6,475,136 B1 | 11/2002 | Forsell |
| 6,485,496 B1 | 11/2002 | Suyker et al. |
| 6,491,704 B2 | 12/2002 | Gifford, III et al. |
| 6,491,705 B2 | 12/2002 | Gifford, III et al. |
| 6,511,490 B2 | 1/2003 | Robert |
| 6,517,556 B1 | 2/2003 | Monassevitch |
| 6,527,701 B1 | 3/2003 | Sayet et al. |

| Patent | Date | Inventor |
|---|---|---|
| 6,547,801 B1 | 4/2003 | Dargent et al. |
| 6,565,582 B2 | 5/2003 | Gifford, III et al. |
| 6,579,301 B1 | 6/2003 | Bales et al. |
| 6,601,604 B1 | 8/2003 | Cooper |
| 6,615,084 B1 | 9/2003 | Cigaina |
| 6,627,620 B1 | 9/2003 | Nielsen |
| 6,630,486 B1 | 10/2003 | Royer |
| 6,632,239 B2 | 10/2003 | Snyder et al. |
| 6,646,628 B2 | 11/2003 | Shirochi et al. |
| 6,676,674 B1 | 1/2004 | Dudai |
| 6,685,668 B1 | 2/2004 | Cho et al. |
| 6,685,963 B1 | 2/2004 | Taupin et al. |
| 6,691,047 B1 | 2/2004 | Fredricks |
| 6,715,731 B1 | 4/2004 | Post et al. |
| 6,729,600 B2 | 5/2004 | Mattes et al. |
| 6,754,527 B2 | 6/2004 | Stroebel et al. |
| 6,767,924 B2 | 7/2004 | Yu et al. |
| 6,811,136 B2 | 11/2004 | Eberhardt et al. |
| 6,820,651 B2 | 11/2004 | Seuret et al. |
| 6,834,201 B2 | 12/2004 | Gillies et al. |
| 6,871,090 B1 | 3/2005 | He et al. |
| 6,889,086 B2 | 5/2005 | Mass et al. |
| 6,916,326 B2 | 7/2005 | Benchetrit |
| 6,921,819 B2 | 7/2005 | Piron et al. |
| 6,924,273 B2 | 8/2005 | Pierce |
| 6,940,467 B2 | 9/2005 | Fischer et al. |
| 6,966,875 B1 | 11/2005 | Longobardi |
| 7,017,583 B2 | 3/2006 | Forsell |
| 7,021,147 B1 | 4/2006 | Subramanian et al. |
| 7,037,344 B2 | 5/2006 | Kagan et al. |
| 7,040,349 B2 | 5/2006 | Moler et al. |
| 7,054,690 B2 | 5/2006 | Imran |
| 7,058,434 B2 | 6/2006 | Wang et al. |
| 7,060,080 B2 | 6/2006 | Bachmann |
| 7,066,486 B2 | 6/2006 | Lee |
| 7,118,526 B2 | 10/2006 | Egle |
| 7,119,062 B1 | 10/2006 | Alvis et al. |
| 7,128,750 B1 | 10/2006 | Stergiopulos |
| 7,144,400 B2 | 12/2006 | Byrum et al. |
| 7,172,607 B2 | 2/2007 | Hofle et al. |
| 7,177,693 B2 | 2/2007 | Starkebsum |
| 7,191,007 B2 | 3/2007 | Desai et al. |
| 7,204,821 B1 | 4/2007 | Clare et al. |
| 7,223,239 B2 | 5/2007 | Schulze et al. |
| 7,238,191 B2 | 7/2007 | Bachmann |
| 7,240,607 B2 | 7/2007 | Fish |
| 7,255,675 B2 | 8/2007 | Gertner et al. |
| 7,263,405 B2 | 8/2007 | Boveja et al. |
| 7,282,023 B2 | 10/2007 | Frering |
| 7,288,064 B2 | 10/2007 | Boustani et al. |
| 7,297,103 B2 | 11/2007 | Jarsaillon et al. |
| 7,299,082 B2 | 11/2007 | Feldman et al. |
| 7,310,557 B2 | 12/2007 | Maschino et al. |
| 7,311,716 B2 | 12/2007 | Byrum |
| 7,311,717 B2 | 12/2007 | Egle |
| 7,314,443 B2 | 1/2008 | Jordan et al. |
| 7,314,636 B2 | 1/2008 | Caseres et al. |
| 7,338,433 B2 | 3/2008 | Coe |
| 7,340,306 B2 | 3/2008 | Barrett et al. |
| 7,351,198 B2 | 4/2008 | Byrum et al. |
| 7,351,240 B2 | 4/2008 | Hassler, Jr. et al. |
| 7,364,542 B2 | 4/2008 | Jambor et al. |
| 7,367,340 B2 | 5/2008 | Nelson et al. |
| 7,367,937 B2 | 5/2008 | Jambor et al. |
| 7,374,565 B2 | 5/2008 | Hassler, Jr. et al. |
| 7,390,294 B2 | 6/2008 | Hassler, Jr. |
| 7,396,353 B2 | 7/2008 | Lorenzen et al. |
| 7,416,528 B2 | 8/2008 | Crawford et al. |
| 7,457,668 B2 | 11/2008 | Cancel et al. |
| 7,481,763 B2 | 1/2009 | Hassler, Jr. et al. |
| 7,500,944 B2 | 3/2009 | Byrum et al. |
| 7,502,649 B2 | 3/2009 | Ben-Haim et al. |
| 7,530,943 B2 | 5/2009 | Lechner |
| 7,594,885 B2 | 9/2009 | Byrum |
| 7,599,743 B2 | 10/2009 | Hassler, Jr. et al. |
| 7,599,744 B2 | 10/2009 | Giordano et al. |
| 7,601,162 B2 | 10/2009 | Hassler, Jr. et al. |
| 7,615,001 B2 | 11/2009 | Jambor et al. |
| 7,618,365 B2 | 11/2009 | Jambor et al. |
| 7,658,196 B2 | 2/2010 | Ferreri et al. |
| 7,670,279 B2 | 3/2010 | Gertner |
| 7,699,770 B2 | 4/2010 | Hassler, Jr. et al. |
| 7,712,470 B2 | 5/2010 | Gertner |
| 7,727,141 B2 | 6/2010 | Hassler, Jr. et al. |
| 7,741,476 B2 | 6/2010 | Lebreton |
| 7,758,493 B2 | 7/2010 | Gingras |
| 7,763,039 B2 | 7/2010 | Ortiz et al. |
| 7,766,815 B2 | 8/2010 | Ortiz |
| 7,771,439 B2 | 8/2010 | Griffiths |
| 7,775,215 B2 | 8/2010 | Hassler, Jr. et al. |
| 7,775,966 B2 | 8/2010 | Dlugos et al. |
| 7,775,967 B2 | 8/2010 | Gertner |
| 7,794,386 B2 | 9/2010 | Brooks |
| 7,811,298 B2 | 10/2010 | Birk |
| 7,824,422 B2 | 11/2010 | Benchetrit |
| 7,828,813 B2 | 11/2010 | Mouton |
| 7,832,407 B2 | 11/2010 | Gertner |
| 7,841,978 B2 | 11/2010 | Gertner |
| 7,844,342 B2 | 11/2010 | Dlugos, Jr. et al. |
| 7,862,502 B2 | 1/2011 | Pool et al. |
| 7,879,068 B2 | 2/2011 | Dlugos et al. |
| 7,951,067 B2 | 5/2011 | Byrum et al. |
| 2001/0011543 A1 | 8/2001 | Forsell |
| 2002/0072780 A1 | 6/2002 | Foley |
| 2002/0091395 A1 | 7/2002 | Gabbay |
| 2002/0095181 A1 | 7/2002 | Beyar |
| 2002/0098097 A1 | 7/2002 | Singh |
| 2002/0139208 A1 | 10/2002 | Yatskov |
| 2002/0183765 A1 | 12/2002 | Adams |
| 2002/0193679 A1 | 12/2002 | Malave et al. |
| 2002/0198548 A1 | 12/2002 | Robert |
| 2003/0014003 A1 | 1/2003 | Gertner |
| 2003/0019498 A1 | 1/2003 | Forsell |
| 2003/0045775 A1 | 3/2003 | Forsell |
| 2003/0045902 A1 | 3/2003 | Weadock |
| 2003/0060873 A1 | 3/2003 | Gertner et al. |
| 2003/0066536 A1 | 4/2003 | Forsell |
| 2003/0073880 A1 | 4/2003 | Polsky et al. |
| 2003/0093157 A1 | 5/2003 | Casares et al. |
| 2003/0100910 A1 | 5/2003 | Gifford, III et al. |
| 2003/0120288 A1 | 6/2003 | Benchetrit |
| 2003/0148995 A1 | 8/2003 | Piron et al. |
| 2003/0158564 A1 | 8/2003 | Benchetrit |
| 2003/0158569 A1 | 8/2003 | Wazne |
| 2003/0181890 A1 | 9/2003 | Schulze et al. |
| 2003/0181917 A1 | 9/2003 | Gertner |
| 2003/0191433 A1 | 10/2003 | Prentiss |
| 2003/0208212 A1 | 11/2003 | Cigaina |
| 2004/0000843 A1 | 1/2004 | East |
| 2004/0044332 A1 | 3/2004 | Stergiopulos |
| 2004/0049209 A1 | 3/2004 | Benchetrit |
| 2004/0059393 A1 | 3/2004 | Policker et al. |
| 2004/0068847 A1 | 4/2004 | Belisle et al. |
| 2004/0106899 A1 | 6/2004 | McMichael et al. |
| 2004/0133219 A1 | 7/2004 | Forsell |
| 2004/0147816 A1 | 7/2004 | Policker et al. |
| 2004/0148034 A1 | 7/2004 | Kagan et al. |
| 2004/0153106 A1 | 8/2004 | Dudai |
| 2004/0162595 A1 | 8/2004 | Foley |
| 2004/0215159 A1 | 10/2004 | Forsell |
| 2004/0230137 A1 | 11/2004 | Mouton |
| 2004/0254536 A1 | 12/2004 | Conlon et al. |
| 2004/0254537 A1 | 12/2004 | Conlon et al. |
| 2004/0260319 A1 | 12/2004 | Egle |
| 2004/0267288 A1 | 12/2004 | Byrum et al. |
| 2004/0267291 A1 | 12/2004 | Byrum et al. |
| 2004/0267292 A1 | 12/2004 | Byrum et al. |
| 2004/0267293 A1 | 12/2004 | Byrum et al. |
| 2004/0267377 A1 | 12/2004 | Egle |
| 2005/0002984 A1 | 1/2005 | Byrum et al. |
| 2005/0038484 A1 | 2/2005 | Knudson et al. |
| 2005/0038498 A1 | 2/2005 | Dubrow et al. |
| 2005/0055039 A1 | 3/2005 | Burnett et al. |
| 2005/0070934 A1 | 3/2005 | Tanaka et al. |
| 2005/0070937 A1 | 3/2005 | Jambor et al. |
| 2005/0100779 A1 | 5/2005 | Gertner |
| 2005/0104457 A1 | 5/2005 | Jordan et al. |
| 2005/0119672 A1 | 6/2005 | Benchetrit |

| | | | | | |
|---|---|---|---|---|---|
| 2005/0119674 A1 | 6/2005 | Gingras | 2007/0125826 A1 | 6/2007 | Shelton |
| 2005/0131383 A1 | 6/2005 | Chen et al. | 2007/0156013 A1 | 7/2007 | Birk |
| 2005/0131485 A1 | 6/2005 | Krundson et al. | 2007/0167672 A1 | 7/2007 | Dlugos et al. |
| 2005/0136122 A1 | 6/2005 | Sadozai et al. | 2007/0167982 A1 | 7/2007 | Gertner et al. |
| 2005/0142152 A1 | 6/2005 | Leshchiner et al. | 2007/0173685 A1 | 7/2007 | Jambor et al. |
| 2005/0143765 A1 | 6/2005 | Bachmann et al. | 2007/0173888 A1 | 7/2007 | Gertner et al. |
| 2005/0143766 A1 | 6/2005 | Bachmann et al. | 2007/0179335 A1 | 8/2007 | Gertner et al. |
| 2005/0154274 A1 | 7/2005 | Jarsaillon et al. | 2007/0185373 A1 | 8/2007 | Tsonton |
| 2005/0171568 A1 | 8/2005 | Duffy | 2007/0185462 A1 | 8/2007 | Byrum |
| 2005/0183730 A1 | 8/2005 | Byrum | 2007/0213836 A1 | 9/2007 | Paganon |
| 2005/0192531 A1 | 9/2005 | Birk | 2007/0218083 A1 | 9/2007 | Brooks |
| 2005/0192601 A1 | 9/2005 | Demarais | 2007/0232848 A1 | 10/2007 | Forsell |
| 2005/0192629 A1 | 9/2005 | Saadat et al. | 2007/0232849 A1 | 10/2007 | Gertner |
| 2005/0216042 A1 | 9/2005 | Gertner | 2007/0233170 A1 | 10/2007 | Gertner |
| 2005/0226936 A1 | 10/2005 | Agerup | 2007/0235083 A1 | 10/2007 | Dlugos |
| 2005/0228415 A1 | 10/2005 | Gertner | 2007/0243227 A1 | 10/2007 | Gertner |
| 2005/0228504 A1 | 10/2005 | Demarais | 2007/0250085 A1 | 10/2007 | Bachmann et al. |
| 2005/0240155 A1 | 10/2005 | Conlon | 2007/0250086 A1 | 10/2007 | Wiley et al. |
| 2005/0240156 A1 | 10/2005 | Conlon | 2007/0255335 A1 | 11/2007 | Herbert et al. |
| 2005/0240279 A1 | 10/2005 | Kagan et al. | 2007/0255336 A1 | 11/2007 | Herbert et al. |
| 2005/0244288 A1 | 11/2005 | O'Neil | 2007/0265598 A1 | 11/2007 | Karasik |
| 2005/0250979 A1 | 11/2005 | Coe | 2007/0265645 A1 | 11/2007 | Birk et al. |
| 2005/0251181 A1 | 11/2005 | Bachmann | 2007/0265646 A1 | 11/2007 | McCoy et al. |
| 2005/0251182 A1 | 11/2005 | Bachmann | 2007/0293716 A1 | 12/2007 | Baker et al. |
| 2005/0267406 A1 | 12/2005 | Hassler, Jr. | 2007/0298005 A1 | 12/2007 | Thibault |
| 2005/0267500 A1 | 12/2005 | Hassler, Jr. | 2008/0009680 A1 | 1/2008 | Hassler, Jr. |
| 2005/0267533 A1 | 12/2005 | Gertner | 2008/0015406 A1 | 1/2008 | Dlugos et al. |
| 2005/0271729 A1 | 12/2005 | Wang | 2008/0015501 A1 | 1/2008 | Gertner |
| 2005/0277899 A1 | 12/2005 | Conlon et al. | 2008/0027269 A1 | 1/2008 | Gartner |
| 2005/0283041 A1 | 12/2005 | Egle | 2008/0027469 A1 | 1/2008 | Bachmann |
| 2005/0288739 A1 | 12/2005 | Hassler, Jr. et al. | 2008/0071306 A1 | 3/2008 | Gertner |
| 2005/0288740 A1 | 12/2005 | Hassler, Jr. et al. | 2008/0097496 A1 | 4/2008 | Chang et al. |
| 2006/0015138 A1 | 1/2006 | Gertner | 2008/0108862 A1 | 5/2008 | Jordan et al. |
| 2006/0020298 A1 | 1/2006 | Camilleri et al. | 2008/0147002 A1 | 6/2008 | Gertner |
| 2006/0041183 A1 | 2/2006 | Massen et al. | 2008/0161717 A1 | 7/2008 | Gertner |
| 2006/0074439 A1 | 4/2006 | Garner et al. | 2008/0161875 A1 | 7/2008 | Stone |
| 2006/0074473 A1 | 4/2006 | Gertner | 2008/0167647 A1 | 7/2008 | Gertner |
| 2006/0089571 A1 | 4/2006 | Gertner | 2008/0167648 A1 | 7/2008 | Gertner |
| 2006/0122147 A1 | 6/2006 | Wohlrab | 2008/0172072 A1 | 7/2008 | Pool et al. |
| 2006/0142700 A1 | 6/2006 | Sobelman et al. | 2008/0188766 A1 | 8/2008 | Gertner |
| 2006/0142790 A1 | 6/2006 | Gertner | 2008/0195092 A1 | 8/2008 | Kim et al. |
| 2006/0161139 A1 | 7/2006 | Levine et al. | 2008/0208240 A1 | 8/2008 | Paz |
| 2006/0161186 A1 | 7/2006 | Hassler, Jr. et al. | 2008/0221598 A1 | 9/2008 | Dlugos et al. |
| 2006/0167531 A1 | 7/2006 | Gertner et al. | 2008/0243071 A1 | 10/2008 | Quijano et al. |
| 2006/0173238 A1 | 8/2006 | Starkebaum | 2008/0249806 A1 | 10/2008 | Dlugos et al. |
| 2006/0173424 A1 | 8/2006 | Conlon | 2008/0250340 A1 | 10/2008 | Dlugos et al. |
| 2006/0183967 A1 | 8/2006 | Lechner | 2008/0250341 A1 | 10/2008 | Dlugos et al. |
| 2006/0189887 A1 | 8/2006 | Hassler, Jr. et al. | 2008/0255403 A1 | 10/2008 | Voegele et al. |
| 2006/0189888 A1 | 8/2006 | Hassler, Jr. et al. | 2008/0255414 A1 | 10/2008 | Voegele et al. |
| 2006/0189889 A1 | 8/2006 | Gertner | 2008/0255425 A1 | 10/2008 | Voegele et al. |
| 2006/0194758 A1 | 8/2006 | Lebreton | 2008/0255459 A1 | 10/2008 | Voegele et al. |
| 2006/0195139 A1 | 8/2006 | Gertner | 2008/0255537 A1 | 10/2008 | Voegele et al. |
| 2006/0197412 A1 | 9/2006 | Rasmussen | 2008/0275294 A1 | 11/2008 | Gertner |
| 2006/0199997 A1 | 9/2006 | Hassler, Jr. et al. | 2008/0275295 A1 | 11/2008 | Gertner |
| 2006/0211912 A1 | 9/2006 | Dlugos et al. | 2008/0275484 A1 | 11/2008 | Gertner |
| 2006/0211913 A1 | 9/2006 | Dlugos et al. | 2008/0281347 A1 | 11/2008 | Gertner |
| 2006/0211914 A1 | 9/2006 | Hassler, Jr. et al. | 2008/0287969 A1 | 11/2008 | Tsonton et al. |
| 2006/0212051 A1 | 9/2006 | Snyder et al. | 2008/0287974 A1 | 11/2008 | Widenhouse et al. |
| 2006/0212053 A1 | 9/2006 | Gertner | 2008/0287976 A1 | 11/2008 | Weaner et al. |
| 2006/0235448 A1 | 10/2006 | Roslin et al. | 2008/0300618 A1 | 12/2008 | Gertner |
| 2006/0246137 A1 | 11/2006 | Hermitte et al. | 2008/0319435 A1 | 12/2008 | Rioux et al. |
| 2006/0247721 A1 | 11/2006 | Maschino et al. | 2009/0054914 A1 | 2/2009 | Lechner |
| 2006/0247722 A1 | 11/2006 | Maschino et al. | 2009/0062825 A1 | 3/2009 | Pool et al. |
| 2006/0252982 A1 | 11/2006 | Hassler, Jr. | 2009/0062826 A1 | 3/2009 | Steffen |
| 2006/0252983 A1 | 11/2006 | Lembo et al. | 2009/0082793 A1 | 3/2009 | Birk |
| 2006/0257488 A1 | 11/2006 | Hubbard | 2009/0118572 A1 | 5/2009 | Lechner |
| 2006/0264699 A1 | 11/2006 | Gertner | 2009/0149874 A1 | 6/2009 | Ortiz et al. |
| 2006/0276812 A1 | 12/2006 | Hill et al. | 2009/0157106 A1 | 6/2009 | Marcotte et al. |
| 2006/0293627 A1 | 12/2006 | Byrum et al. | 2009/0157107 A1 | 6/2009 | Kierath et al. |
| 2007/0015954 A1 | 1/2007 | Dlugos | 2009/0157113 A1 | 6/2009 | Marcotte et al. |
| 2007/0015955 A1 | 1/2007 | Tsonton | 2009/0171375 A1 | 7/2009 | Coe et al. |
| 2007/0015956 A1 | 1/2007 | Crawford et al. | 2009/0171378 A1 | 7/2009 | Coe et al. |
| 2007/0016231 A1 | 1/2007 | Jambor et al. | 2009/0171379 A1 | 7/2009 | Coe et al. |
| 2007/0016262 A1 | 1/2007 | Gross et al. | 2009/0187202 A1 | 7/2009 | Ortiz et al. |
| 2007/0027356 A1 | 2/2007 | Ortiz | 2009/0192404 A1 | 7/2009 | Ortiz et al. |
| 2007/0027358 A1 | 2/2007 | Gertner et al. | 2009/0192415 A1 | 7/2009 | Ortiz et al. |
| 2007/0044655 A1 | 3/2007 | Fish | 2009/0192533 A1 | 7/2009 | Dlugos, Jr. et al. |
| 2007/0077292 A1 | 4/2007 | Pinsky | 2009/0192534 A1 | 7/2009 | Ortiz et al. |
| 2007/0078476 A1 | 4/2007 | Hull, Sr. et al. | 2009/0192541 A1 | 7/2009 | Ortiz et al. |

| | | | | | | |
|---|---|---|---|---|---|---|
| 2009/0198261 A1 | 8/2009 | Schweikert | FR | 2688693 | 9/1993 | |
| 2009/0202387 A1 | 8/2009 | Dlugos, Jr. et al. | FR | 2769491 | 4/1999 | |
| 2009/0204131 A1 | 8/2009 | Ortiz et al. | FR | 2783153 | 3/2000 | |
| 2009/0204132 A1 | 8/2009 | Ortiz et al. | FR | 2797181 | 2/2001 | |
| 2009/0209995 A1 | 8/2009 | Byrum et al. | FR | 2799118 | 4/2001 | |
| 2009/0216255 A1 | 8/2009 | Coe et al. | FR | 2823663 | 10/2002 | |
| 2009/0220176 A1 | 9/2009 | Fusco | FR | 2855744 | 12/2004 | |
| 2009/0222031 A1 | 9/2009 | Axelsson | FR | 2921822 | 4/2009 | |
| 2009/0222065 A1 | 9/2009 | Dlugos, Jr. et al. | GB | 1174814 | 12/1969 | |
| 2009/0228063 A1 | 9/2009 | Dlugos, Jr. et al. | GB | 2090747 | 7/1982 | |
| 2009/0228072 A1 | 9/2009 | Coe et al. | JP | 57-171676 | 10/1982 | |
| 2009/0270904 A1 | 10/2009 | Birk et al. | JP | 1-67309 | 4/1989 | |
| 2009/0306462 A1 | 12/2009 | Lechner | JP | 2-019147 | 1/1990 | |
| 2010/0010291 A1 | 1/2010 | Birk et al. | JP | 2-132104 | 11/1990 | |
| 2010/0049224 A1 | 2/2010 | Vargas | JP | 3-105702 | 11/1991 | |
| 2010/0087843 A1 | 4/2010 | Bertolote et al. | JP | 11-244395 | 9/1999 | |
| 2010/0099945 A1 | 4/2010 | Birk et al. | JP | 2003-526410 | 9/2003 | |
| 2010/0100079 A1 | 4/2010 | Berkcan | JP | 2005-131380 | 5/2005 | |
| 2010/0145378 A1 | 6/2010 | Gertner | JP | 2005-334658 | 12/2005 | |
| 2010/0152532 A1 | 6/2010 | Marcotte | SE | 8503144 | 12/1986 | |
| 2010/0168508 A1 | 7/2010 | Gertner | WO | WO 86/00079 | 1/1986 | |
| 2010/0185049 A1 | 7/2010 | Birk et al. | WO | WO 86/00912 | 2/1986 | |
| 2010/0191265 A1 | 7/2010 | Lau et al. | WO | WO 89/11701 | 11/1989 | |
| 2010/0191271 A1 | 7/2010 | Lau et al. | WO | WO 90/00369 | 1/1990 | |
| 2010/0204647 A1 | 8/2010 | Gertner | WO | WO 92/20349 | 11/1992 | |
| 2010/0204723 A1 | 8/2010 | Gertner | WO | WO 94/02517 | 2/1994 | |
| 2010/0217071 A1 | 8/2010 | Ricol | WO | WO 96/33751 | 1/1996 | |
| 2010/0226988 A1 | 9/2010 | Lebreton | WO | WO 98/35639 | 8/1998 | |
| 2010/0228080 A1 | 9/2010 | Tavori et al. | WO | WO 98/35640 | 8/1998 | |
| 2010/0234682 A1 | 9/2010 | Gertner | WO | WO 00/00108 | 1/2000 | |
| 2010/0249803 A1 | 9/2010 | Griffiths | WO | WO 00/01428 | 1/2000 | |
| 2010/0280310 A1 | 11/2010 | Raven | WO | WO 00/09047 | 2/2000 | |
| 2010/0305397 A1 | 12/2010 | Birk et al. | WO | WO 00/09049 | 2/2000 | |
| 2010/0312046 A1 | 12/2010 | Lau et al. | WO | WO 00/15158 | 3/2000 | |
| 2010/0312147 A1 | 12/2010 | Gertner | WO | WO 00/66196 | 11/2000 | |
| 2010/0324358 A1 | 12/2010 | Birk et al. | WO | WO 01/10359 | 2/2001 | |
| 2010/0324359 A1 | 12/2010 | Birk | WO | WO 01/12078 | 2/2001 | |
| 2011/0201874 A1 | 8/2011 | Birk et al. | WO | WO 01/41671 | 6/2001 | |
| FOREIGN PATENT DOCUMENTS | | | WO | WO 01/47435 | 7/2001 | |
| | | | WO | WO 01/47575 | 7/2001 | |
| CN | 1367670 | 9/2002 | WO | WO 01/49245 | 7/2001 | |
| DE | 4225524 | 2/1994 | WO | WO 01/52777 | 7/2001 | |
| DE | 10020688 | 12/2000 | WO | WO 01/68007 | 9/2001 | |
| EP | 0119596 | 9/1984 | WO | WO 01/85071 | 11/2001 | |
| EP | 0230747 | 8/1987 | WO | WO 02/05753 | 1/2002 | |
| EP | 0416250 | 3/1991 | WO | WO 02/09792 | 2/2002 | |
| EP | 0611561 | 8/1994 | WO | WO 02/19953 | 3/2002 | |
| EP | 0695558 | 2/1996 | WO | WO 02/26317 | 4/2002 | |
| EP | 0876808 | 11/1998 | WO | WO 02/053093 | 7/2002 | |
| EP | 1036545 | 9/2000 | WO | WO 02/065948 | 8/2002 | |
| EP | 1072282 | 1/2001 | WO | WO 02/096326 | 12/2002 | |
| EP | 1105073 | 6/2001 | WO | WO 03/007782 | 1/2003 | |
| EP | 1396242 | 3/2004 | WO | WO 03/055420 | 7/2003 | |
| EP | 1396243 | 3/2004 | WO | WO 03/057092 | 7/2003 | |
| EP | 1491167 | 12/2004 | WO | WO 03/059215 | 7/2003 | |
| EP | 1491168 | 12/2004 | WO | WO 03/077191 | 9/2003 | |
| EP | 1529502 | 5/2005 | WO | WO 03/101352 | 12/2003 | |
| EP | 1547549 | 6/2005 | WO | WO 03/105732 | 12/2003 | |
| EP | 1574189 | 9/2005 | WO | WO 2004/014245 | 2/2004 | |
| EP | 1600183 | 11/2005 | WO | WO 2004/019671 | 3/2004 | |
| EP | 1602346 | 12/2005 | WO | WO 2004/108025 | 12/2004 | |
| EP | 1704833 | 9/2006 | WO | WO 2004/112563 | 12/2004 | |
| EP | 1719480 | 11/2006 | WO | WO 2005/007232 | 1/2005 | |
| EP | 1736123 | 12/2006 | WO | WO 2005/009305 | 2/2005 | |
| EP | 1736195 | 12/2006 | WO | WO 2005/067994 | 7/2005 | |
| EP | 1736202 | 12/2006 | WO | WO 2005/072195 | 8/2005 | |
| EP | 1743605 | 1/2007 | WO | WO 2005/087147 | 9/2005 | |
| EP | 1829504 | 9/2007 | WO | WO 2005/094447 | 10/2005 | |
| EP | 1829505 | 9/2007 | WO | WO 2005/112888 | 12/2005 | |
| EP | 1829506 | 9/2007 | WO | WO 2006/040647 | 4/2006 | |
| EP | 1967168 | 9/2008 | WO | WO 2006/049725 | 5/2006 | |
| EP | 1992315 | 11/2008 | WO | WO 2006/083885 | 8/2006 | |
| EP | 2074970 | 7/2009 | WO | WO 2006/108203 | 10/2006 | |
| EP | 2074971 | 7/2009 | WO | WO 2007/067206 | 6/2007 | |
| EP | 2074972 | 7/2009 | WO | WO 2007/081304 | 7/2007 | |
| EP | 2095796 | 9/2009 | WO | WO 2007/106727 | 9/2007 | |
| EP | 2095798 | 9/2009 | WO | WO 2007/114905 | 10/2007 | |
| EP | 2191796 | 6/2010 | WO | WO 2007/145638 | 12/2007 | |
| FR | 1566202 | 5/1969 | WO | WO 2008/063673 | 5/2008 | |

| WO | WO 2008/134755 | 11/2008 |
| --- | --- | --- |
| WO | WO 2009/050709 | 4/2009 |
| WO | WO 2009/132127 | 10/2009 |
| WO | WO 2009/136126 | 11/2009 |
| WO | WO 2010/042493 | 4/2010 |

OTHER PUBLICATIONS

Adrian et al.; "Mechanism of Pancreatic Polypeptide Release in Man." The Lancet; pp. 161-163; Jan. 22, 1977.

Anson; "Shape Memory Alloys—Medical Applications," Source: Materials World, vol. 7, No. 12, pp. 745-747, Dec. 1999.

Asakawa et al; "Antagonism of Ghrelin Receptor Reduces Food Intake and Body Weight Gain in Mice"; Gut.; V.52; pp. 947-952; 2003.

Baggio et al. "Biology of Incretins: GLP-1 and GIP"; Gastroenrology; V. 132; pp. 2131-2157; 2007.

Ballantyne; "Peptide YY(1-36) and Peptide YY(3-36): Part I. Distribution, Release, and Actions"; Obesity Surgery; V.16; pp. 651-658; 2006.

Ballantyne; "Peptide YY(1-36) and Peptide YY(3-36): Part II. Changes after Gastrointestinal Surgery and Bariatric Surgery"; Obesity Surgery; V.16; pp. 795-803; 2006.

Berne et al; "Physiology"; V. 5; pp. 55-57, 210, 428, 540, 554, 579, 584, 591; 2004.

BioEnterics Lap-Band Adjustable Gastric Banding System, Inamed Health, pub., pp. 1-115; Aug. 28, 2003.

Boulant et al.; "Cholecystokinin in Transient Lower Oesophageal Sphincter Relaxation Due to Gastric Distension in Humans"; Gut.; V. 40; pp. 575-581; 1997.

Bradjewin et al.; "Dose Ranging Study of the Effects of Cholecystokinin in Healthy Volunteers"; J. Psychiatr. Neurosci.; V. 16 (2); pp. 91-95; 1991.

Burdyga et al.; "Cholecystokinin Regulates Expression of Y2 Receptors in Vagal Afferent Neurons Serving the Stomach"; The Journal of Neuroscience; V. 28; No. 45; pp. 11583-11592; Nov. 5, 2008.

Chaptini et al.; "Neuroendocrine Regulation of Food Intake"; Current Opinion in Gastroenterology; V. 24; pp. 223-229; 2008.

Chaudhri; "Can Gut Hormones Control Appetite and Prevent Obesity?" Diabetes Care; V. 31; Supp 2; pp. S284-S289; Feb. 2008.

Cohen et al.; "Oxyntomodulin Suppresses Appetite and Reduces Food Intake in Humans"; J. Clin. Endocrinol. Metab.; V. 88; No. 10; pp. 4696-4701; 2003.

Corno et al.; "A new implantable device for telemetric control of pulmonary blood flow"; New ideas; 10 pages.

Corno et al.; "FlowWatchTM in clipped and inclipped position"; Interact Cardio Vase Thorac Surg 2002; 1:46-49; Copyright @ 2002 The European Asociation for Cardio-thoracic Surgery; 1 page.

Cummings et al.; "Plasma Ghrelin Levels After Diet-Induced Weight Loss or Gastric Bypass Sugery"; N. Engl J. Med; V. 346, No. 21; pp. 1623-1630; May 23, 2002.

Cummings; "Gastrointestinal Regulation of Foot Intake"; The Food Journal of Clinical Investigation; V. 117, N. 1; pp. 13-23; Jan. 2007.

Dakin et al.; "Oxyntomodulin Inhibits Food Intake in the Rat"; Endocrinology; V. 142; No. 10; pp. 4244-4250; 2001.

Dakin et al.; "Peripheral Oxyntomodulin Reduces Food Intake and Body Weight gain in Rats"; Endocrinology; V. 145; No. 6; pp. 2687-2695; Jun. 2004.

Davison; "Activation of Vagal-Gastric Mechanoreceptors by Cholecystokinin"; Proc. West. Pharmocol. Soc.; V. 29; pp. 363-366; 1986.

De Waele et al.; "Endoscopic Volume Adjustment of Intragastric Balloons for Intolerance"; Obesity Surgery; V. 11; pp. 223-224; 2001.

De Waele et al.; "Intragastric Balloons for Preoperative Weight Reduction"; Obesity Surgery; V. 58; pp. 58-60; 2001.

Desai et al.; "Molecular Weight of Heparin Using 13C Nuclear Magnetic Resonance Spectroscopy" Journal of Pharmaceutical Science, V. 84, I 2; 1995, Abstract only.

Doldi et al.; "Intragastric Balloon: Another Option for Treatment of Obesity and Morbid Obesity"; Hepato-Gastroenterology; V. 51, N. 55; pp. 294-307; Jan.-Feb. 2004.

Doldi et al.; "Treatment of Morbid Obesity with Intragastric Balloon in Association with Diet"; Obesity Surgery; V. 10, pp. 583-587; 2000.

Doldi et al; "Intragastric Balloon in Obese Patients"; Obesity Surgery; V. 10, 578-581; 2000.

Ekblad et al.; "Distribution of Pancreatic Peptide and Peptide-YY"; Peptides; V. 23; pp. 251-261; 2002.

El Khoury et al.; "Variation in Postprandial Ghrelin Status Following Ingestion of High-Carbohydrate, High Fat, and High Protein Meals in Males"; Ann Nutr Metab; V. 50; pp. 260-269; 2006.

Galloro et al; "Preliminary Endoscopic Technical Report of an New Silicone Intragastric Balloon in the Treatment of Morbid Obesity"; Obesity Surgery; V. 9, pp. 68-71; 1999.

GinShiCel MH Hydroxy Propyl Methyl Cellulose, Web Page http://www.ginshicel.cn/MHPC.html, Nov. 12, 2008.

Girard; "The incretins: From the concept to their use in the treatment of type 2 diabetes. Part A: Incretins: Concept and physiological functions"; Diabetes and Metabolism; V. 34; pp. 550-559; 2008.

Greenough et al.; "Untangling the Effects of Hunger, Anxiety, and Nausea on Energy Intake During Intravenous Cholecystokinin Octapeptide (CCK-8) Infusion"; Physiology & Behavior; V. 65, No. 2; pp. 303-310; 1998.

Grise et al.; "Peptide YY Inhibits Growth of Human Breast Cancer in Vitro and in Vivo"; Journal of Surgical Research; V. 82; pp. 151-155; 1999.

Grundy; "Signaling the State of the Digestive Tract"; Autonomic Neuroscience: Basic and Clinical; V. 125; pp. 76-80; 2006.

Grundy; "Vagal Control of Gastrointestinal Function"; Bailliere's Clinical Gastroenterology; V. 2; No. 1; pp. 23-43; 1988.

Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.

Hameed et al.; "Gut hormones and appetite control." Oral Diseases; V. 15; pp. 18-26; 2009.

Hassan et al.; "Effects of Adjuvants to Local Anesthetics on Their Duration III Experimental Studies of Hyaluronic Acid" Abstract Pub Med [Acta Anesthesiol Scand.; 29 (4): 384-8], 1 page; May 1985.

Hodson et al.; "Management of Obesity with the New Intragastric Balloon"; Obesity Surgery; V. 11, pp. 327-329, 2001.

Holzer; "Gastrointestinal Afferents as Targets of Novel Drugs for the Treatment of Functional Bowel Disorders and Visceral Pain"; European Journal of Pharmacology; V. 429; pp. 177-193; 2001.

Houpt; "Gastrointestinal Factors in Hunger and Satiety." Neuroscience and Behavioral Reviews; V. 6; pp. 145-164; 1982.

Jones; "Molecular, pharmacological, and clinical aspects of liraglutide, a oncedaily human GLP-1 analogue"; Molecular and Cellular Endocrinology; V. 297; pp. 137-140; 2009.

Kerem et al.; "Exogenous Ghrelin Enhances Endocrine and Exocrine Regeneration in Pancreatectomized Rats"; J Gastrointest Surg.; V.13; pp. 775-783, 2009.

Kesty et al.; "Hormone-based therapies in the regulation of fuel metabolism and body weight"; Expert Opin. Biol. Ther.; V. 8; No. 11; pp. 1733-1747; 2008.

Kissileff et al.; "Peptides that Regulate Food Intake: Cholecystokinin and Stomach Distension Combine to Reduce Food Intake in Humans"; Am. J. Physiol. Regul. Integr. Comp. Physiol; V. 285; pp. 992-998; 2003.

Kojima et al.; "A role for pancreatic polypeptide in feeding and body weight regulation." Peptides; V. 28; pp. 459-463; 2007.

Kulicke et al. "Visco-Elastic Propeerties of Sodium Hyaluronate Solutions," American Institute of Physics; pp. 585-587; 2008.

Lap-Band AP System Adjustable Gastric Banding System With OmniformTM Design: Directions for Use (DFU); Allergan, 16 pages; 2009.

Le Roux et al.; "Gut Hormone Profiles Following Bariatric Surgery Favor an Anorectic State, Facilitate Weight Loss, and Improve Metabolic Parameters"; Ann. Surg; V. 243; No. 1; pp. 108-114; Jan. 2006.

Liu et al.; "Adjuvant Hormonal Treatment With Peptide YY or Its Analog Decreases Human Pancreatic Carcinoma Growth"; The American Journal of Surgery; V. 171; pp. 192-196; Jan. 1996.

Mathus-Vliegen et al. "Intragastric Balloons for Morbid Obesity: Results, Patient Tolerance and Balloon Life Span"; Br. J. Surg.; V. 77, No. 7, pp. 76-79; Jan. 1990.

Mathus-Vliegen et al. "Treating Morbid and Supermorbid Obesity" International Journal of Gastroenterology; V. 5, No. 1, pp. 9-12; 2000.

Medeiros et al.; "Processing and metabolism of Peptide-YY: Pivotal roles of Dipeptidase-IV, Aminopeptidase-P, and Endopeptidase-24.11"; Endocrinology; V. 134, No. 5; pp. 2088-2094; 1994.

Naslund et al. "Pranidal subcutaneous injections of glucagon-like peptide-1 cause weight loss in obese human subjects"; British Journal of Nutrition; V. 91; pp. 439-446; 2004.

Potier et al.; "Protein, amino acids, and the control of food intake"; Current Opinion in Clinical Nutrition and Metabolic Care; V. 12; pp. 54-58; 2009.

Qjan et al.; "Pulmonary delivery of a GLP-1 receptor agonist, BMS-686117"; International Journal of Pharmaceutics; V. 366; pp. 218-220; 2008.

Rang et al.; "Pharmacology"; V. 5; pp. 203, 397, 402, 524; 2004.

Raybould et al.; "Integration of Postprandial Gastrointestinal Tract: Role of CCK and Sensory Pathways"; Annals of New York Academy of Science; pp. 143-156; 1994.

Renshaw et al. "Peptide YY: A Potential Therapy for Obesity"; Current Drug Targets; V. 6; pp. 171-179; 2005.

Sannino et al.; "Crosslinking of Cellulose Derivatives and Hyaluronic Acid with Water-Soluble Carbodiimide" Polymer 46; pp. 11206-11212; 2005.

Shechter et al.; "Reversible PEGylation of peptide YY3-36 prolongs its inhibition of food intake in mice"; FEBS Letters; V. 579; pp. 2439-2444; 2005.

Silver et al.; "Physical Properties of Hyaluronic Acid and Hydroxypropylmethylcellulose in Solution: Evaluation of Coating Abillity" Journal of Applied Biomaterials, V. 5; pp. 89-98, 1994.

Small et al.; "Gut hormones and the control of appetite"; TRENDS in Endocrinology and Metabolism; V. 15. No. 6; pp. 259-263; Aug. 2004.

Stanley et al.; "Gastrointestinal Satiety Signals III. Glucagon-like Peptide 1, oxyntomodulin, peptide YY, and pancreatic polypeptide"; Am. J. Physiol Gastrointest Liver Physiol; V. 286; pp. 693-697; 2004.

Tezel; "The Science of Hyaluronic Acid Dermal Fillers," Journal of Cosmetic and Laser Therapy (2008) 10: pp. 35-42.

Tolhurst et al.; "Nutritional regulation of glucagon-like peptide1 secretion"; J. Physiol.; V. 587, No. 1; pp. 27-32; 2009.

Totte et al.; "Weight Reduction by Means of Intragastric Device: Experience with the Bioenterics Intragastric Balloon"; Obesity Surgery; V. 11, pp. 519-523; 2001.

Tough et al.; "$Y_4$ Receptors Mediate the Inhibitory Responses of Pancreatic Polypeptide in Human and Mouse Colon Mucosa"; The Journal of Pharmacology and Experimental Therapeutics; V. 319, No. 1; pp. 20-30; 2006.

Tseng et al; "Peptide YY and cancer: Current findings and potential clinical applications"; Peptides; V. 23; pp. 389-395; 2002.

Valassi et al.; "Neuroendocrine control of food intake"; Nut. Metab. & Cariovasc. Disease; V. 18; pp. 158-168; 2008.

Van Der Lely et al.; "Biological, Physiological, Pathophysiological Aspects of Ghrelin"; Endocrine Reviews; V. 25, No. 3; pp. 426-457; 2004.

Verdich et al. "A Meta-Analysis of the Effect of Glucagon-Like-Peptide-1 (7-36) Amide on ad Libitum Energy Intake in Humans"; J. Clin. Endocrinal. Metab. V. 86; pp. 4382-4389; Sep. 2001.

Wahlen et al.; "The BioEnterics Intragastric Balloon (BIB): How to Use It"; Obesity Surgery; V. 11; pp. 524-527; 2001.

Wang et al.; "Plasma Ghrelin Modulation in Gastric Band Operation and Sleeve Gastrectomy"; Obes. Surg.; pp. 357-362; 2008.

Weiner et al.; "Preparation of Extremely Obese Patients for Laparoscopic Gastric Banding by Gastric Balloon Therapy"; Obesity Surgery; V. 9, pp. 261-264, 1999.

Wynne et al.; "Subcutaneous Oxyntomodulin Reduces Body Weight in Overweight and Obese Subjects: A Double-Blind Randomized, Controlled Trial"; Diabetes; V. 54; pp. 2390-2395; 2005.

Yuzuriha et al.; "Gastrointestinal Hormones (anorexigenic peptide YY and orexigenic ghrelin) influence neural tube development"; FASEB J.; V. 21; pp. 2108-2112; 2007.

Brown et al; "Symmetrical Pouch Dilation After Laparoscopic Adjustable Gastric Banding: Incidence and Management"; Obesity Surgery; V. 18, pp. 1104-1108; 2008.

Ceelen et al.; "Surgical Treatment of Severe Obesity With a Low-Pressure Adjustable Gastric Band: Experimental Data and Clinical Results in 625 Patients"; Annals of Surgery; V. 237, No. 1; pp. 10-16; 2003.

Dixon et al.; "Pregnancy After Lap-Band Surgery: Management of the Band to Achieve Healthy Weight Outcomes"; Obesity Surgery; V. 11, pp. 59-65; 2001.

Helioscopie Product Insert for Heliogast, pp. 1-11 (undated).

Neary et al.; "Peptide YY(3-36) and Glucagon-Like Peptide-$1_{(7-36)}$ Inhibit Food Intake Additively"; Endocrinology; V.146; pp. 5120-5127; 2005.

Padidela et al.; "Elevated basal and post-feed glucagon-like petide 1 (GLP-1) concentrations in the neonatel period"; European Journal of Endocrinology; v. 160; pp. 53-58; 2009.

Shi et al.; "Sexually Dimorphic Responses to Fat Loss After Caloric Restriction or Surgical Lipectomy"; Am. J. Physiol. Endocrinol. Metab.; V. 293; E316-E326; 2007.

Xanthakos et al.; "Bariatric Surgery for Extreme Adolescent Obesity: Indications, Outcomes, and Physiologic Effects on the Gut-Brain Axis"; Pathophysiology; V. 15; pp. 135-146; 2008.

\* cited by examiner

CLOSURE SYSTEM FOR TUBULAR ORGANS

RELATED APPLICATIONS

This application is a continuation of U.S. patent application Ser. No. 10/591,869, entitled "CLOSURE SYSTEM FOR TUBULAR ORGANS" filed on Jun. 27, 2007 which is now U.S. Pat. No. 7,811,299, which was the National Stage of International Application No. PCT/IB05/50822, entitled "CLOSURE SYSTEM FOR TUBULAR ORGANS" filed on Mar. 5, 2005, which claims priority to International Application No. PCT/CH04/000136, entitled "CLOSURE SYSTEM FOR TUBULAR ORGANS" filed on Mar. 8, 2004, the entire disclosures of each of these applications are incorporated herein by reference.

FIELD OF THE INVENTION

The present invention relates to surgical devices for adjusting the diameter of tubular organs such as the esophagus, the stomach, the colon or the urethra. Such devices may be used as sphincters (e.g. as anal or urinary sphincters) or for the control of obesity. More particularly, the present invention relates to surgically implantable adjustable rings for encircling said tubular organs.

BACKGROUND OF THE INVENTION

Surgical devices for adjusting the diameter of tubular organs have been disclosed in the prior art, for example, in patent documents U.S. Pat. No. 5,658,298, U.S. Pat. No. 6,601,604, FR 2 823 663, WO 01/85071 and WO 03/059215.

In particular, the device disclosed in International Publication No. WO 03/059215 has an open ring shape that comprises a first and second end parts and that is designed to be closed around a tubular organ at the two end parts. A closure system adjusts the diameter of the tubular organ by forming the ring into a loop. The first end part of the ring is shaped like a sleeve and is designed to receive the second end part of the ring, the main axis of the sleeve being defined along a direction that is substantially perpendicular to the main direction of the first end part. The second part of the ring comprises instead a hook-shaped extension that is adapted to capture the edge of the second end part of the sleeve, and thereby to secure the ring in a closed position.

SUMMARY OF THE INVENTION

An object of the present invention is to provide a closure system improved over the devices in the prior art.

This and other objects of the present invention are achieved by providing a surgically implantable ring that can be adjusted in diameter. In one embodiment, a surgically adjustable ring constructed according to the principles of the present invention comprises an open ring body that is designed to constrict a tubular organ and that includes a closure system having a first and a second end parts. The first end part includes a sleeve that has a first and a second portion and that is designed to receive the second end part of the closure system. A locking protrusion extends from the second end part and is adapted to engage an aperture in the sleeve, thereby securing the ring in a closed position.

BRIEF DESCRIPTION OF THE DRAWINGS

The above and other objects and advantage of the present invention will be apparent upon consideration of the following detailed description, taken in conjunction with the accompanying drawings, in which like reference numerals refer to like parts throughout, and in which.

DETAILED DESCRIPTION OF THE INVENTION

An embodiment of the invention will be discussed in greater detail hereinafter.

Figure 1:
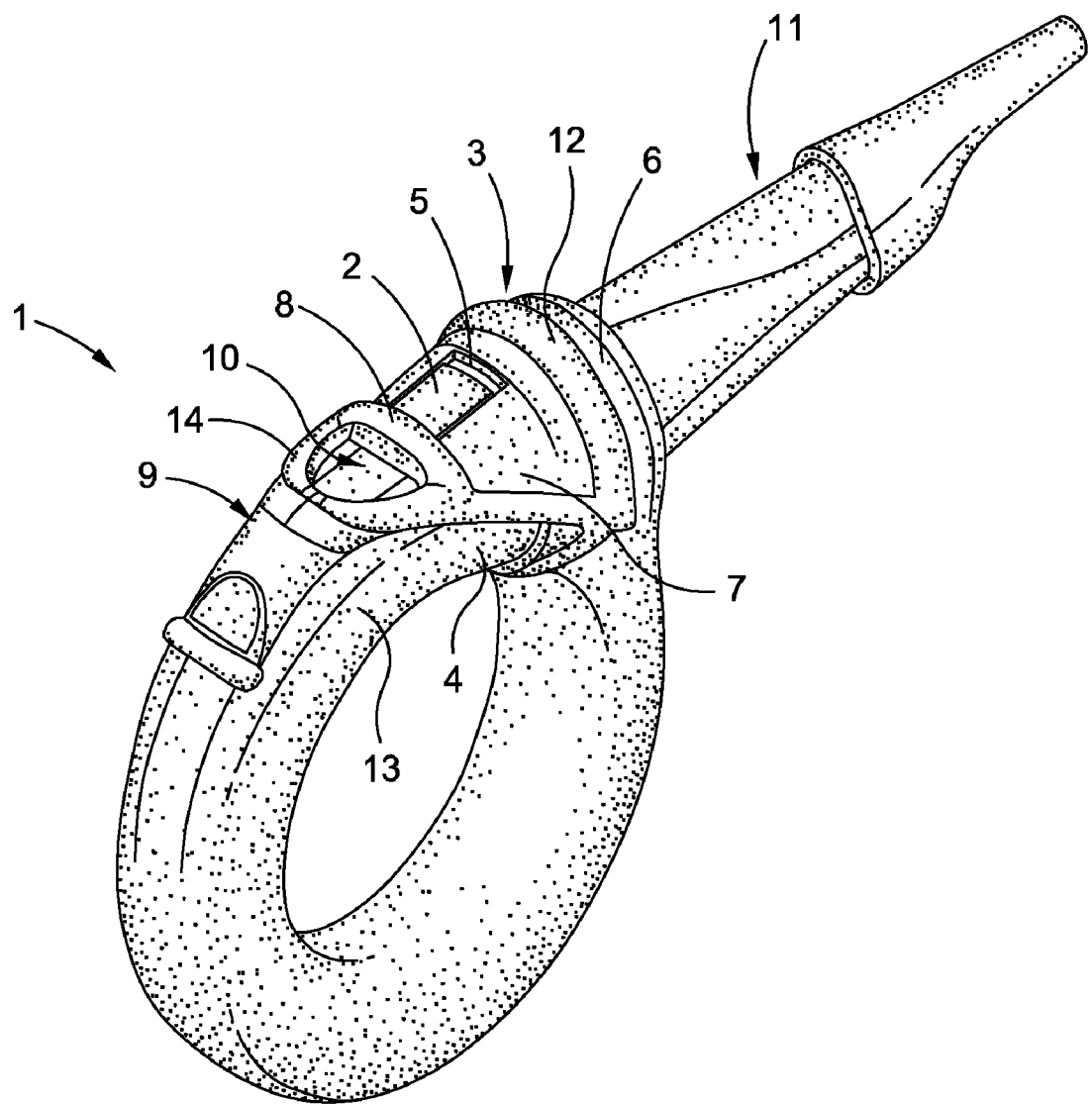
FIG. 1 is a perspective view of an embodiment of the invention in a closed position.
Figure 2:
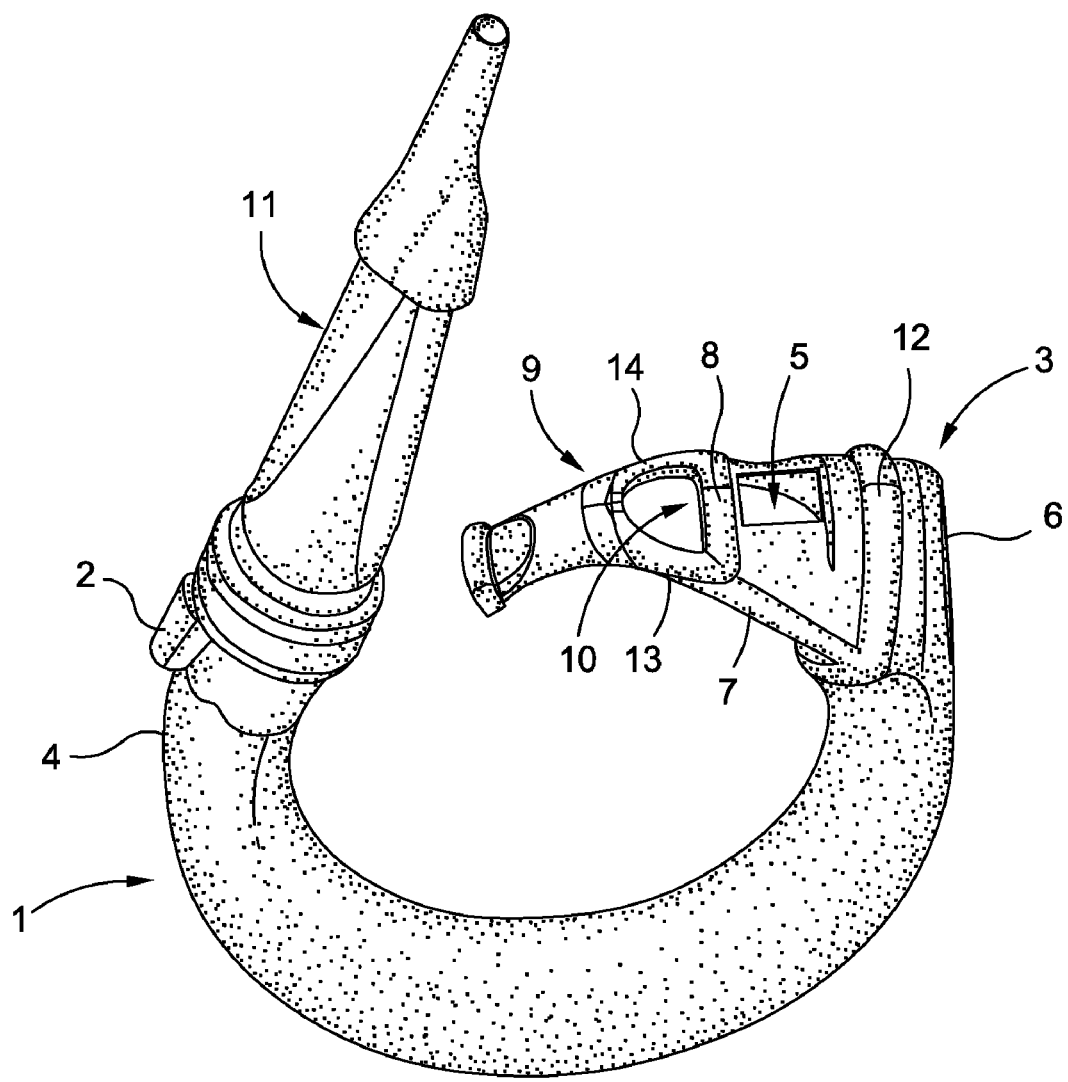
FIG. 2 is a perspective view of the embodiment of FIG. 1 in an open position.

Referring to FIGS. 1 and 2, adjustable ring 1 comprises a closure system having a first end part 3 and a second end part 4.

Ring 1 may be manufactured from any suitable material, for example, from a biocompatible elastomeric material. The external part of ring 1 may be more rigid than the internal part, which has an internal diameter that is adjustable.

First end part 3 is shaped like a sleeve designed to receive second end part 4, while second end part 4 has an extension 11 containing adjusting means, for instance, a wire which can be pulled or pushed in order to adjust the diameter of ring 1.

The sleeve on first end part 3 includes first end portion 6, which is reinforced by a flange 12, and second end portion 7, which contains aperture 5 designed to receive and efficiently retain protrusion 2, and which engages second end part 4.

For the purpose of closing or opening ring 1, second end portion 7 of the sleeve is provided with an extension defining flexible tab 9, which contains opening 10 situated close to the aperture 5. The presence of the opening 10 in tab 9 provides several advantages, in particular the accidental opening of the closure system is prevented in situations where tab 9 has to support forces, tending to bend tab 9 in the direction of extension 11. Such forces may be due to the movement of the patient, or of the organs of the patient, or to the fluid or bolus passing through the tubular organ.

The area between aperture 5 and opening 10 is reinforced by flange 8. The other sides of the opening 10 are also reinforced by flanges 13, 14.

The shape of protrusion 2 is designed to closely match the shape of flange 8.

The invention is of course not limited to the above described embodiment. In another embodiment, opening 10 may be replaced by a portion that is more flexible than the remaining part of tab 9. Such a more flexible portion may be obtained with different techniques, for example, by making that portion thinner than the rest of tab 9. In still another embodiment, the second portion of the sleeve may partially overlap the second part of the closure system when the ring is in the closed position.

The invention may be advantageously used in a variety of applications, for instance, as a sphincter or as a gastric ring.

What is claimed is:

1. A surgically implantable adjustable gastric ring for constricting an organ, the adjustable gastric ring comprising:
   a ring having a first end part and a second end part, the ring being designed to be closed around the organ;
   the first end part including a sleeve being designed to receive the second end part, the sleeve including a first aperture; and
   the second end part including a locking protrusion adapted to engage the first aperture in the sleeve, thereby securing the ring in a closed position;
   wherein the sleeve includes a second aperture and a first reinforcement flange and a second reinforcement flange, the second aperture disposed substantially parallel to the first aperture, and the first reinforcement flange being located adjacent to and in between the first aperture and the second aperture, wherein the sleeve has a first portion and a second portion, the sleeve having a tab extending from the second portion, the sleeve being disposed in a substantially perpendicular direction in relation to the direction of the first end part, and wherein the second reinforcement flange is positioned between the first aperture and the first portion of the sleeve.

2. The adjustable gastric ring of claim 1, wherein the locking protrusion and the first aperture comprise a closure system.

3. The adjustable gastric ring of claim 1, wherein the second aperture comprises a flexible portion of the sleeve, the flexible portion being more flexible than the remaining portion of the sleeve.

4. The adjustable gastric ring of claim 1, wherein the first reinforcement flange is disposed transversally to the external perimeter of the ring.

5. The adjustable gastric ring of claim 1, wherein the ring is made of a biocompatible elastomeric material.

6. A surgically implantable adjustable gastric ring closure system comprising:
   a ring;
   a first end part including:
      a sleeve having a first portion;
      a second portion defining a first aperture;
      a third portion defining a flexible portion being more flexible than the first portion of the sleeve, the second portion positioned between the first and third portions;
      a first reinforcement flange disposed adjacent to and in between the first aperture and the flexible portion;
      a second reinforcement flange positioned at the first portion, the first aperture positioned between the first reinforcement flange and the second reinforcement flange; and
   a second end part including a locking element, the first end part and the second end part positioned at opposite ends of the ring.

7. The closure system of claim 5, wherein the locking element comprises a protrusion extending from the second end part.

8. The closure system of claim 6, wherein the flexible portion comprises a second aperture.

9. The closure system of claim 8, wherein the second aperture remains substantially unfilled when the closure system is in a closed position.

10. The closure system of claim 6, wherein the second end part and at least one of the portions of the first end part are substantially perpendicular to one another.

11. The closure system of claim 6, wherein the flexible portion has adjacent sides and a side reinforcement flange is positioned at one of the adjacent sides.

12. The closure system of claim 6, further comprising adjusting means to adjust a diameter of the ring.

13. The closure system of claim 6, wherein the third portion includes a tab made of a flexible material.

14. A surgically implantable adjustable gastric ring comprising:
   a first end part and a second end part of the ring, the ring being designed to be closed around a tubular organ towards the first end part of the ring and the second end part of the ring by a closure system to adjust the diameter of the tubular organ by forming a loop, the closure system including a first aperture and a locking protrusion;
   the first end part of the ring including a sleeve having a first end portion and a second end portion and a first reinforcement flange and a second reinforcement flange, the first aperture positioned on the sleeve between the first reinforcement flange and the second reinforcement flange;
   the sleeve designed to receive the second end part of the ring, the sleeve main axis being disposed in a substantially perpendicular direction in relation to the direction of the first end part of the ring;
   the second end part of the ring including the locking protrusion, the locking protrusion being adapted to engage the first aperture to hold the sleeve and thereby secure the ring in a closed position;
   wherein the first end portion of the sleeve includes a tab extending away from the second end portion of the sleeve; and
   wherein the tab comprises a flexible portion being more flexible than the remaining part of the tab such as to prevent an accidental opening of the closure system.

15. The adjustable gastric ring of claim 14, wherein the flexible portion comprises a second aperture.

16. The adjustable gastric ring of claim 15, wherein the second reinforcement flange is positioned adjacent to the second aperture.

17. The adjustable gastric ring of claim 14, wherein the flexible portion is made thinner than the tab.

18. The adjustable gastric ring of claim 14, wherein the flexible portion is positioned close to the first aperture.

19. The adjustable gastric ring of claim 14, wherein the flexible portion is adjacent to the first aperture.

* * * * *